(12) United States Patent
Borschneck

(10) Patent No.: US 7,670,308 B2
(45) Date of Patent: Mar. 2, 2010

(54) MEDICAL SPLINTING APPARATUS AND METHODS FOR USING THE SAME

(76) Inventor: Anthony G. Borschneck, 770 Flower Ash La., Redding, CA (US) 96003

( * ) Notice: Subject to any disclaimer, the term of this patent is extended or adjusted under 35 U.S.C. 154(b) by 0 days.

(21) Appl. No.: 12/009,479

(22) Filed: Jan. 18, 2008

(65) Prior Publication Data

US 2008/0177208 A1 Jul. 24, 2008

Related U.S. Application Data

(60) Provisional application No. 60/897,165, filed on Jan. 23, 2007.

(51) Int. Cl.
  *A61F 5/00* (2006.01)
  *E05D 11/10* (2006.01)
  *E05D 15/00* (2006.01)
  *E05D 15/22* (2006.01)
  *E05D 7/08* (2006.01)
  *E05D 7/00* (2006.01)

(52) U.S. Cl. .................. 602/16; 602/1; 602/5; 602/21; 602/26; 602/27; 16/334; 16/368; 16/369; 49/188; 49/388; 49/397

(58) Field of Classification Search .................. 602/16, 602/5, 1, 26, 27, 21; 16/334, 369; 49/188, 49/388, 397
See application file for complete search history.

(56) References Cited

U.S. PATENT DOCUMENTS

| 4,350,153 A | 9/1982 | Borschneck |
|---|---|---|
| 4,463,750 A | 8/1984 | Borschneck |
| 4,608,971 A | 9/1986 | Borschneck |
| 4,781,180 A * | 11/1988 | Solomonow .................. 602/16 |
| 4,941,465 A | 7/1990 | Borschneck |
| 6,203,511 B1 * | 3/2001 | Johnson et al. ................ 602/16 |
| 2004/0188302 A1 * | 9/2004 | Rogers, Jr. ................... 206/438 |
| 2006/0142681 A1 * | 6/2006 | Suarez et al. .................. 602/23 |
| 2007/0010772 A1 * | 1/2007 | Ryan ............................ 602/26 |

* cited by examiner

*Primary Examiner*—Patricia M Bianco
*Assistant Examiner*—Tarla R. Patel
(74) *Attorney, Agent, or Firm*—R. Michael West

(57) ABSTRACT

An articulated, adjustable, and lockable alignment arm, and associated extensions and accessories, which are user manipulable to model the size and shape of the fractured limb of a patient in the field. The alignment arm includes a first elongated arm segment, a second elongated arm segment, and connector means for interconnecting the first segment to the second segment through respective pivotal receivers having normal axes of rotation. The alignment arm is adjusted for proper orientation by setting it over the injury, and then locking the arm into a selected orientation which models the patient's limb around the area of the injury. Next, first and second arm extenders and protective end pads are used to expand the effective size of the alignment arm to form a custom splint structure. Lastly, the splint structure is secured to the patient's injured limb through the use of flexible cravats.

18 Claims, 7 Drawing Sheets

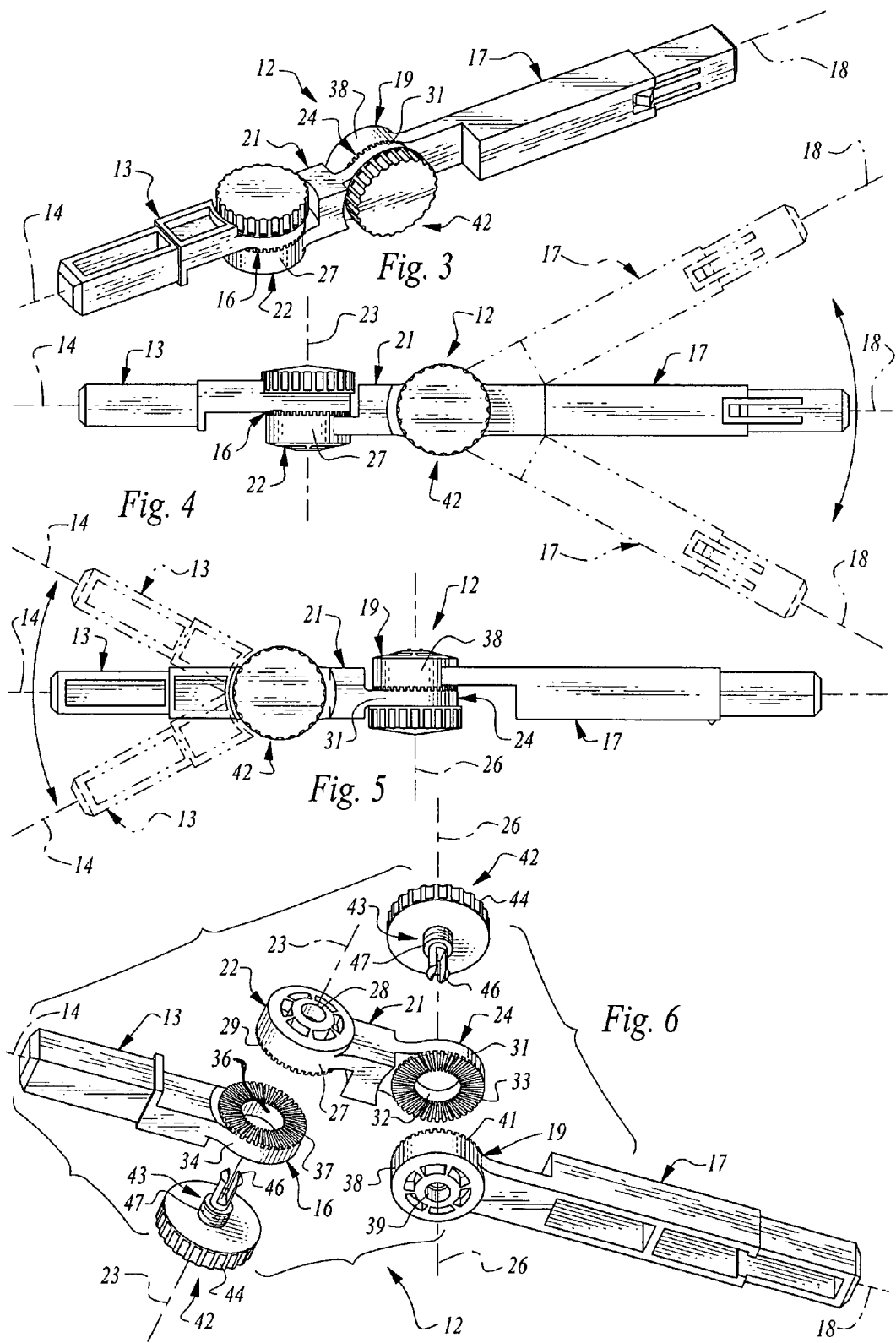

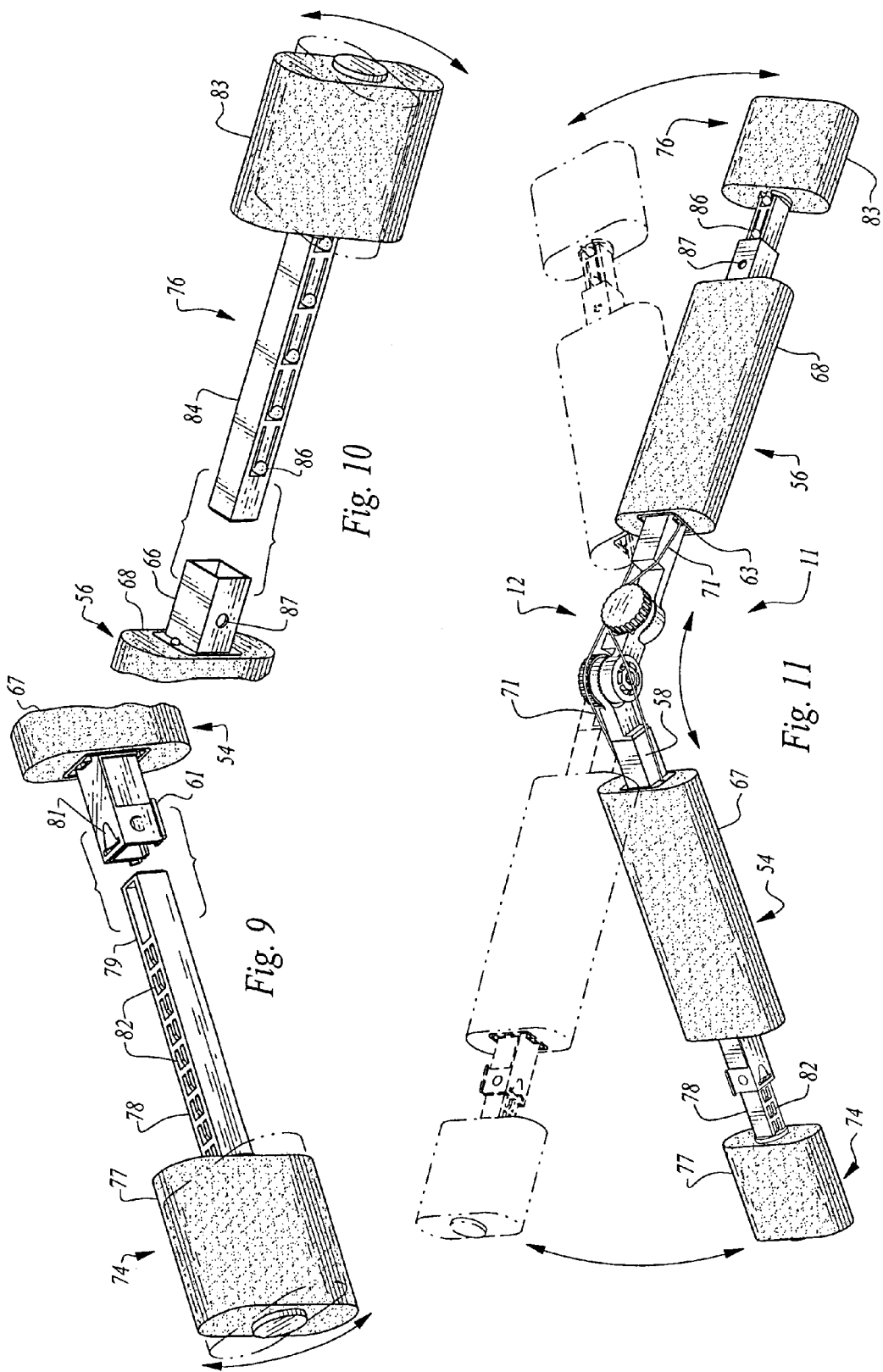

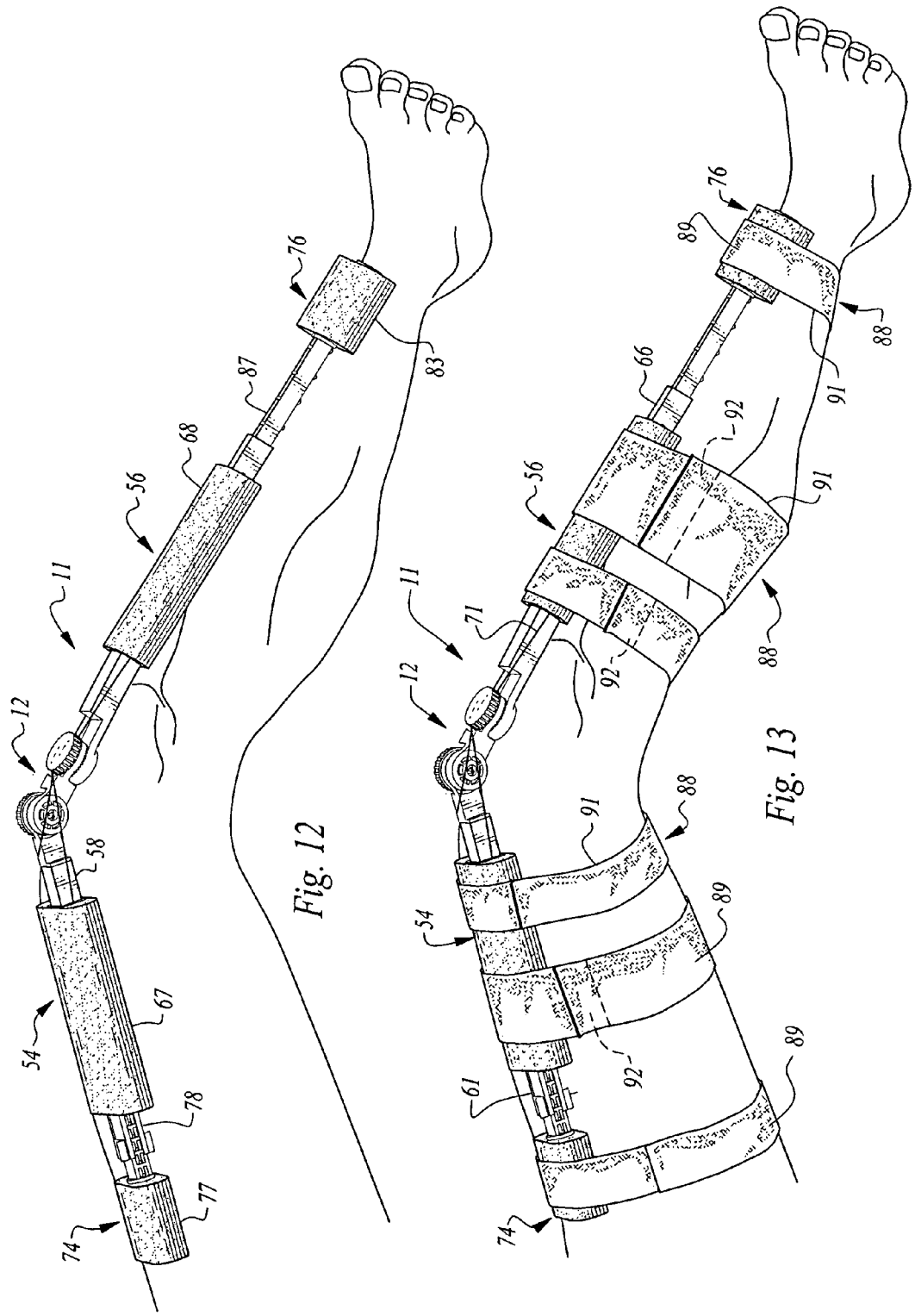

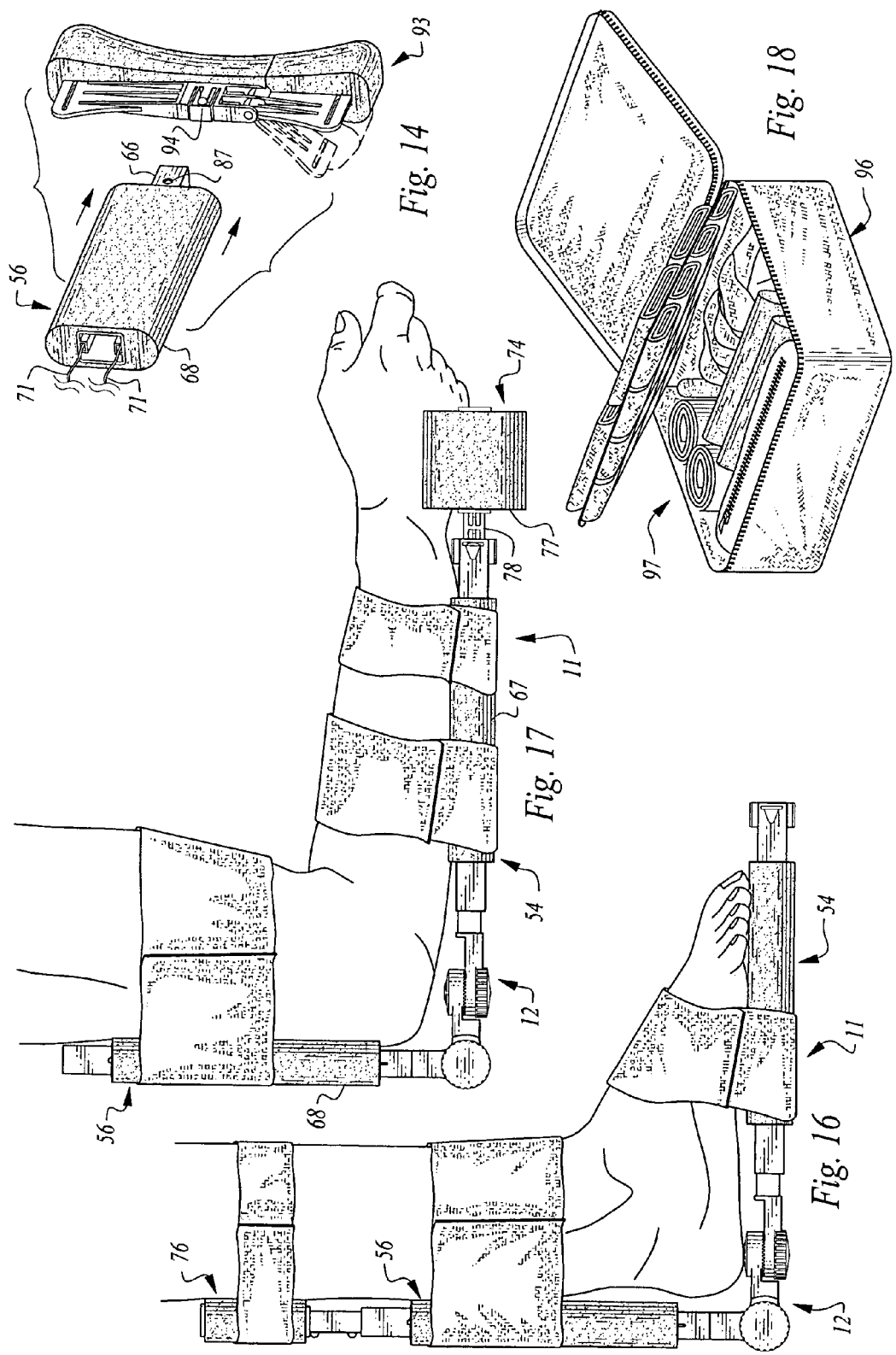

MEDICAL SPLINTING APPARATUS AND METHODS FOR USING THE SAME

PRIORITY CLAIM

Pursuant to the provisions of 35 U.S.C. §119(e)(1), Applicant claims the priority of U.S. Provisional Patent Application Ser. No. 60/897,165, filed Jan. 23, 2007.

BACKGROUND OF THE INVENTION

1. Field of the Invention

The invention relates generally to improvements in apparatus and methods providing medical splinting for fractured or broken human limbs, joints, and body parts. More particularly, the invention pertains to an articulated, adjustable, and lockable alignment arm, and associated extensions and accessories. These components are user manipulable in the field, to create a rigid, padded, structural model which emulates the shape of the fractured limb of a patient. By securing the structural model and the limb together with fabric cravats, the injured patient may be transported comfortably and safely to a medical center.

2. Description of the Prior Art

Medical splinting apparatus is used in treating and transporting patients who have suffered a bone or joint injury, such as a fracture or dislocation. The task of the splint is to stabilize the broken or fractured body parts quickly and with minimal pain and discomfort to the patient. One recognized problem stems from the wide variety of injuries encountered, ranging from a broken arm or leg, to a dislocated shoulder. Each of these injuries calls for a splint having a different size and configuration. Consequently, the paramedic or doctor must have splints of different sizes and configurations available in the field, so they can be adapted to the patient's injury and used effectively.

Other problems encountered include patient discomfort and possible aggravation of the injury resulting from improper splinting. The splints must be designed so they can be applied with minimal discomfort to the patient, who is likely already in pain. At the same time, an effective splint must stabilize the joint or fracture so that further injury does not occur either during transport or as a consequence of unexpected patient movement during transport to a medical facility.

Where the injury has occurred in the field or under the conditions of a traumatic accident, the job of splinting the injury and transporting the patient to a hospital in a remote location is particularly challenging. The patient may have to be extracted from a damaged motor vehicle, or moved up a steep cliff, even before primary transport has begun. Thus, the splinting apparatus must be lightweight, quick to apply to the patient, and effective in immobilizing the broken or fractured body part.

In U.S. Pat. No. 4,608,971, issued to Borschneck, an emergency leg splint is shown. This device was designed as a single or double leg traction splint for treatment of a fractured femurs. This splint worked well clinically. In addition, its use necessitated that the body of the splint extended beyond the patient's feet. This extended length prevented unrestricted use in confined spaces, such as helicopters and ambulances used in patient transport.

There remained a need for a device that would both splint and apply traction to injured limbs, in circumstances where both femurs were fractured. It was also desirable that such a splint would be confined entirely within the lower body profile, to make patient transport easier and safer. Lastly, a review of the anatomy and pathophysiology of fractured femurs and related pelvic structures indicated an improvement was needed in the proximal end of the splint, where it rested against the ischial tuberosity. The ischial tuberosity is located at the distal end of the pelvis, and is distal to the perineal body in both the male and female sexes. These skeletal hard points protect the perineum and form the base platform for the lower torso when a human sits.

To address these needs, an ischial perineal cushion for emergency traction splint was developed. This cushion is shown in U.S. Pat. No. 4,941,465, granted to Borschneck. The cushion, located at the proximal end, seats the splint comfortably and reliably against the ischial perineal protuberances. The distal end of the splint does not extend beyond the lower body profile, facilitating easier transport of the patient. In those respects, the traction splint of the '465 patent represented an improvement in the performance and safety of the prior art splints used to stabilize human limbs, joints, and body parts.

Nevertheless, current medical requirements indicate the need for an improved splint device or system that is small, light and compact, for transport to remote and difficult to reach accident locations. There is also a need for a splint which is radiolucent, particularly in the region of the patient's injury. This feature affords the option of leaving the device intact on the patient during X-ray, CAT scan and M.R.I studies. And, there remains a need for a device which can be configured to splint any fracture of any limb, joint or body part of any size adult or child. More specifically there is a need for a single splint apparatus or system, that can be adapted to accommodate a variety of fractures or dislocations with a minimum of pain and/or movement.

SUMMARY OF THE INVENTION

The present invention provides for improvements in splints used for transporting injured patients from a field location to a treatment facility. Such improvements include: (1) splints with radiolucent properties around and along the region of the injury, thus allowing X-ray, Cat Scan and MRI imaging of the injury without the need for removing the splint; (2) a portable splint kit which may be packaged, transported, disassembled, or reassembled in the field, quickly and efficiently; (3) splint assemblies which provide both a splinting function and apply a quantifiable traction force to one or two broken femurs; and, (4) a splint modeling system having adjustment and fixation features allowing the splinting of any limb, joint or body part on any human of any size or age.

The heart of the splint modeling system is an articulated, adjustable, and lockable, alignment arm. The alignment arm is comprised of two arm segments, each having one respective end pivotally attached to a respective end of an intermediate connector body. The axes for the pivotal attachments are perpendicular with respect to each other. The arm segments may be independently adjusted and selectively locked into a plurality of rotational positions about a respective axis. In use, the alignment arm is shaped adjacent and parallel to any fractured bone or joint, thereby producing a modeled structure having the same configuration and orientation as the injured limb. The procedure affords accurate splinting of the fractured member without movement or production of pain. Rotating locking knobs on the connector body ensures that the alignment arm retains the shape of the injury. Once the alignment arm is locked into the desired configuration, the arm segments are lengthened through the use of arm extenders fitted with padded material. End pads may also be installed into the free ends of the arm extenders. The assembly is then gently placed on the limb or body, and secured in position with two or more fabric cravats of variable lengths and widths. This affords safe movement of the patient, while securing the injured limbs and joints of the patient in the same position they were found by medical personnel.

The outer surface of the flexible cravats is provided with a dynamic composite elasticized loop fabric, marketed under the trademark BREATH-O-PRENE. The inner surface is provided with an opened cell foam material, embedded with nano-crystals of silver. For the purpose of securing the cravats around the limb and the modeled splint, one end of each cravat includes a short length of hook Velcro sewn thereon. These cravats create a quick, secure closure member, binding the limb to the splint structure.

Another application for certain components of the invention is to splint, for example, leg injuries also needing a pre-determined amount of traction. In this application, a bilateral traction splint assembly is provided, including a spring pulley and cable structure, entirely mounted and enclosed within in a telescopic housing at the distal end of the assembly. The same arm extenders used in the articulated splint are coupled together to form a straight splint shaft, extending between a base cushion seated against the user's ischial tuberosity at the proximate end of the assembly, and an ankle cravat secured to the user's ankle at the distal end of the assembly. The splint shaft is padded on both lateral surfaces lying along the inner sides the user's leg, providing enhanced patient comfort.

A carrying case is also provided, housing a kit comprising a disassembled bilateral traction splint, an articulated alignment arm, padded arm extenders, end pads, and a plurality of fabric cravats of varying widths and lengths. In the hands of properly trained medical personnel, this kit is capable of quickly and correctly providing a traction splint, if needed, for fractured femurs, or providing a modeled splint for stabilizing a limb extending from the body of any sized adult or child.

BRIEF DESCRIPTION OF THE DRAWINGS

FIG. 3 is a perspective view of the articulated alignment arm;

FIG. 4 is a top plan view of the alignment arm, showing a range of rotation for a first arm segment;

FIG. 5 is a side elevational view of the alignment arm, showing a range of rotation for a second arm segment;

FIG. 6 is an exploded perspective view of the alignment arm, including the first and second arm segments and the intermediate connector means;

FIG. 9 is a perspective view, showing the rotational adjustable feature of an end pad and a first type of coupler means between the pad and the extender;

FIG. 10 is a perspective view, showing the same rotational feature for the other end pad and a second type of coupler means between the pad and the extender;

FIG. 11 is a perspective view showing a typical assembled splint, the phantom representation showing an alternative configuration for the splint;

FIG. 12 is a perspective view showing the splint of FIG. 11 placed over the patient's injured limb;

FIG. 13 is a perspective view, showing the splint of FIG. 12 attached to the patient's limb through the use of a plurality of fabric cravats;

FIG. 14 is a perspective view of an articulated ischio-perineal cushion;

FIG. 16 is a side elevational view of a patient with a foot or ankle injury, fitted with the splint;

FIG. 17 is a side elevational view of a patient with an elbow or arm injury, fitted with the splint; and, FIG. 18 is a perspective view of an open carrying case, displaying the components of the splint kit in a stowed condition.

DETAILED DESCRIPTION OF THE PREFERRED EMBODIMENT

Figures 1, 2:
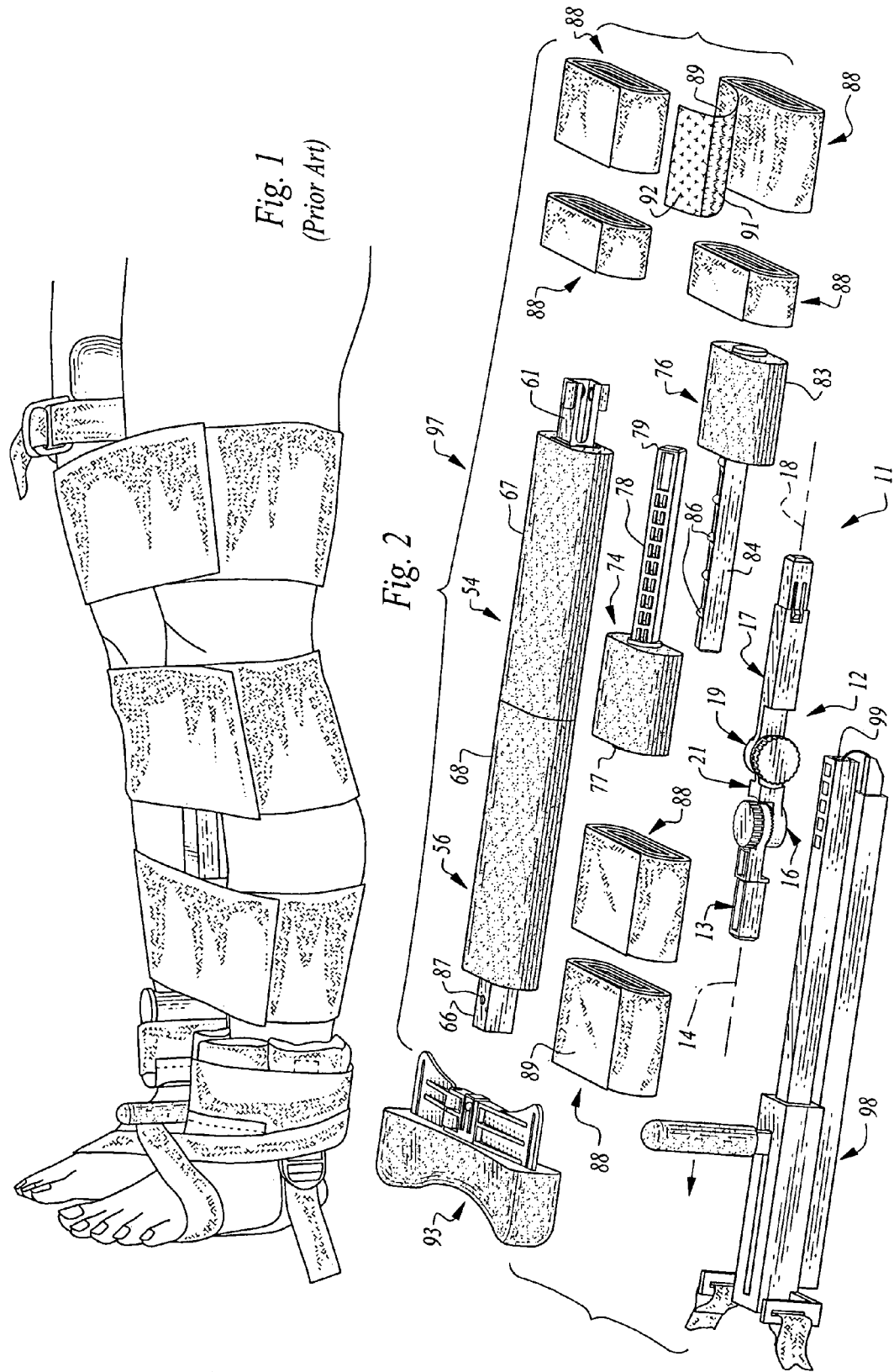
FIG. 1 is a side elevational view, showing a prior art leg splint.
FIG. 2 is a perspective view, showing the assembly of various components comprising the portable splint kit of the present invention.

The splint apparatus 11 of the present invention comprises an articulated alignment arm 12, for modeling the orientation and configuration of an injured human limb. Alignment arm 12 includes a first elongated arm segment 13 having a longitudinal axis 14 and a respective pivot end 16, and a second elongated arm segment 17 having a longitudinal axis 18 and a respective pivot end 19. Alignment arm 12 also includes a dual-axis connector body 21 for interconnecting first arm segment 13 to second arm segment 17. Connector body 21 is provided with a first receiver 22 adapted to couple with respective pivot end 16 of first arm segment 13 and lock it at a first selected orientation about a first transverse axis 23. Connector body 21 is also provided with a second receiver 24 adapted to couple with respective pivot end 19 of second arm segment 17 and lock it at a second selected orientation about a second transverse axis 26. As is evident from FIGS. 4, 5, and 6, first transverse axis 23 and second transverse axis 26 are perpendicular with respect to each other, and each transverse axis is also perpendicular to the longitudinal axis of a respective arm segment.

First receiver 22 is provided with a disc portion 27, a first receiver pivot aperture 28, and a plurality of ribs 29 extending radially from the pivot aperture 28. Similarly, second receiver 24 is provided with a disc portion 31, a second receiver pivot aperture 32, and a plurality of ribs 33 extending radially from the pivot aperture 32. For the purpose of coupling with first receiver 22, pivot end 16 of first arm segment 13 includes a respective disc portion 34 provided with a segment pivot aperture 36 and a plurality of ribs 37 extending radially from pivot aperture 36. Similarly, pivot end 19 of second arm segment 17 includes a respective disc portion 38 provided with a segment pivot aperture 39 and a plurality of ribs 41 extending radially from segment pivot aperture 39.

A pair of threaded fasteners 42 is provided for selectively securing the receivers of the connector body in interlocking relation to the pivot ends of the first and second arm segments. Fasteners 42 comprise a shaft 43 having a knob 44 on one end, a resilient barb 46 on the other end, and threads 47 therebetween. Complementary threads are also provided in first receiver pivot aperture 28 and in second arm segment pivot aperture 39.

Fasteners 42 are installed so that the threads in the respective apertures are in a location remote from the knobs 44, so that when the knobs are rotated in clockwise fashion, contingent ribs of the arm segments and the connector body are drawn together in interlocking relation. The location of the threads can easily be reversed, between the pivot apertures in the segments and the connector body, providing identical results and functionality. The barbs 46 act to keep the arm segments and the connector body together, even when the fasteners 42 are completely disengaged from the threads in the apertures. This prevents the loss of parts and assures quick assembly and use of the splint apparatus 11.

Figure 15:
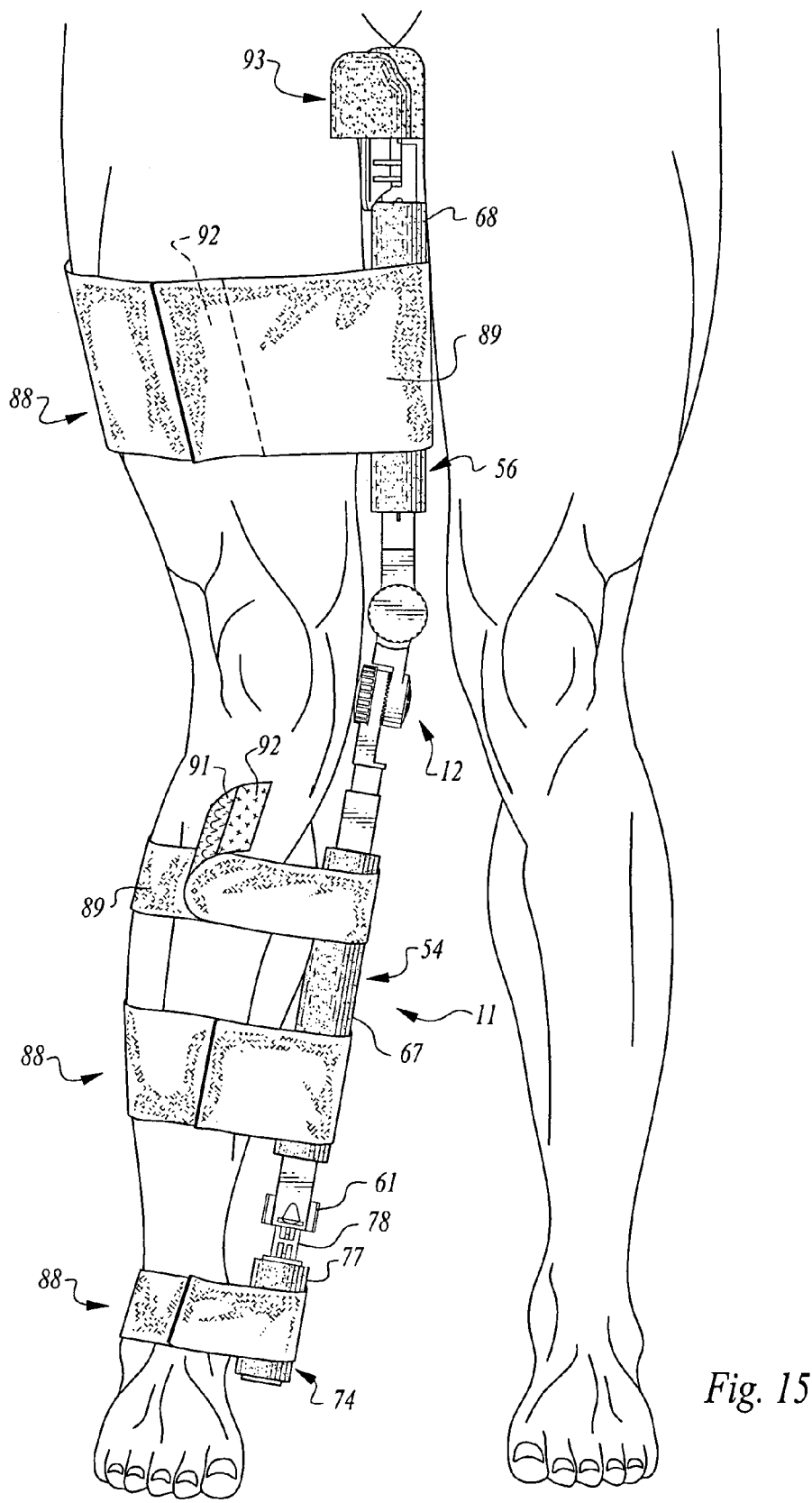
FIG. 15 is a top plan view of a patient with a straight leg injury, such as a dislocated knee, fitted with the field adjustable splint of the present invention.

In use of the articulated alignment arm 12, the medical personnel first loosens the knobs 44, so the arm segments 13 and 17 can be pivotally adjusted through a range of motion as generally depicted in FIGS. 4 and 5. The alignment arm is then placed over the critical area of the patient's injured limb or body part. This critical area will vary, depending upon the nature of the injury. For example, in FIG. 7, a bent leg injury such as a bone fracture calls for the alignment arm to be placed generally over the patient's knee cap. In FIG. 15, another bent leg injury such as a dislocated knee requires that the alignment arm be place along the medial side of the knee cap. FIG. 16 shows the alignment arm 12 in a pre-determined 90° locked orientation, located at the patient's heel for ankle and foot injuries. As yet another example, FIG. 17 shows the alignment arm 12 in a pre-determined 90° locked orientation, located at the patient's elbow, for elbow and lower arm injuries.

Other types of limb and body part injuries which can be accommodated by the splint apparatus include, without limitation, dislocated shoulder injuries, forearm injuries, fracture dislocations of the knee, and straight leg knee injuries. Each of these injuries may call for different orientations and placements for the splint apparatus 11, depending upon the circumstances of the injury and the condition of the limb as the medical personnel finds the patient. Therefore, no attempt will be made to describe each and every potential orientation and placement for the splint apparatus 11, as these will vary widely and the specific applications are within the experience and training of the medical personnel to determine in the field.

Figures 7, 8:
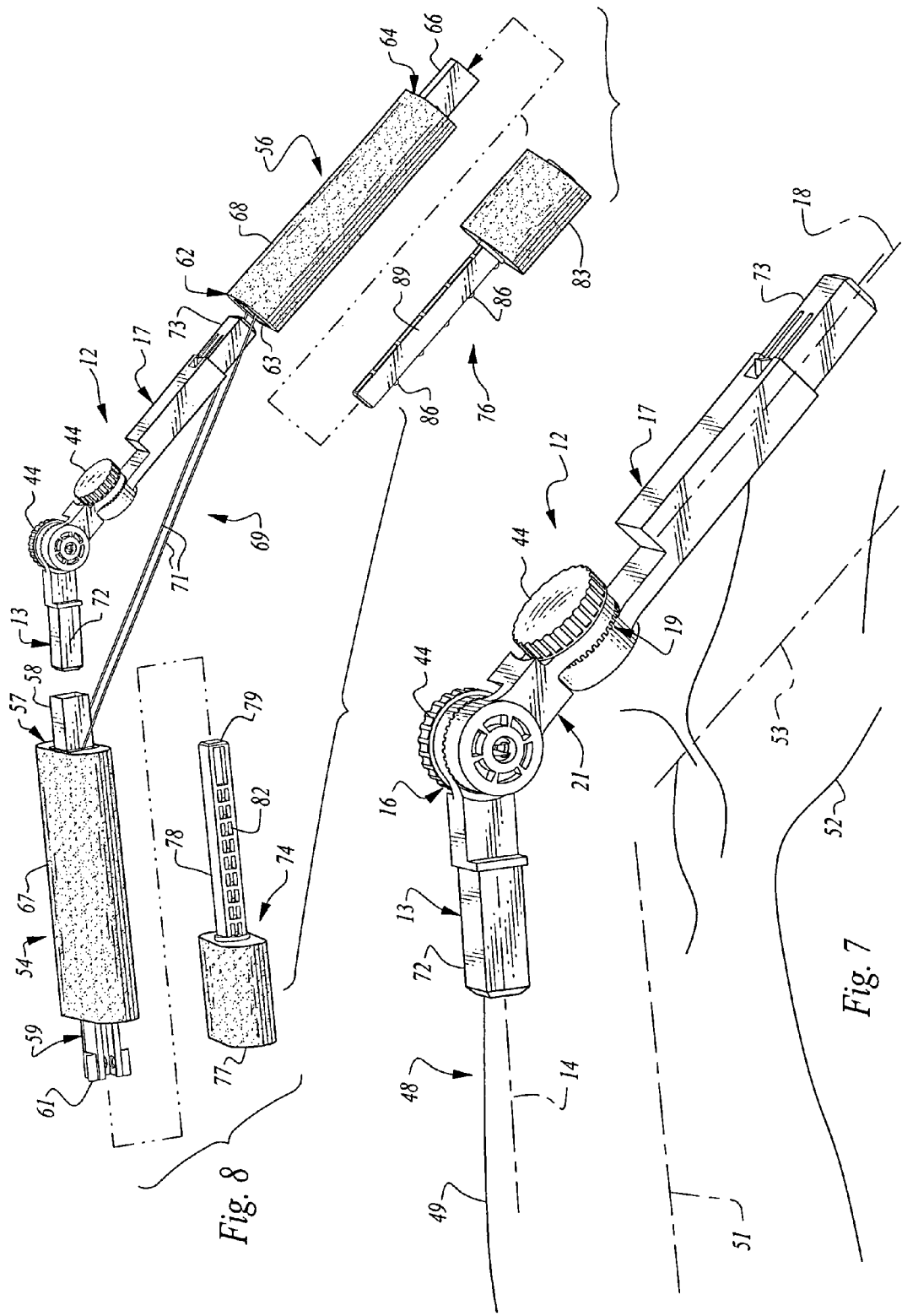
FIG. 7 is a perspective view, showing the alignment arm placed on the injured portion of the patient's leg for modeling.
FIG. 8 is an exploded perspective view of the alignment arm being assembled with arm extenders and protective end pads.

Returning to FIG. 7, it is assumed that the injured human limb 48 has a first part 49 with a longitudinal axis 51, and a second part 52 with a longitudinal axis 53. It is further assumed that the human limb 48 has been found by the medical personnel in the same orientation as shown in FIG. 7, upon first encountering the patient. Alignment arm 12 is manually adjusted by the medical personnel so that a first selected orientation places the longitudinal axis 14 of first arm segment 13 in generally parallel relation to the longitudinal axis 51 of first part 49. Then, alignment arm 12 is manually adjusted so that a second selected orientation places the longitudinal axis 18 of second arm segment 17 and the longitudinal axis 53 of the second part 52 in generally parallel relation. Lastly, knobs 44 are both rotated clockwise to secure and lock the alignment arm in an orientation which emulates the configuration of the injured limb 48, in and around the critical area where the first part and the second part join. Now that the alignment arm has a fixed configuration, the rest of the splint apparatus 11 can be assembled and then secured to the injured limb.

For the purpose of expanding the physical size of the alignment arm so it can become a useful splint, a first elongated arm extender 54 and a second elongated arm extender 56 are provided. First arm extender 54 has one end 57 provided with a coupler 58 and another end 59 provided with a coupler 61. Second arm extender 56 has one end 62 provided with a coupler 63 and another end 64 provided with a coupler 66. Foam padding 67 is provided entirely around and along arm extender 54, between couplers 58 and 61. Similarly, foam padding 68 is provided entirely around and along arm extender 56, between couplers 63 and 66.

Resilient and flexible bias means 69, for drawing arm extenders 54 and 56 together, interconnects one end 57 with one end 62. Bias means 69 is preferably comprised of two stretchable cords 71 being stretchable to the extent shown in FIG. 8. With the alignment arm removed from the injured limb, coupler 58 on one end 57 of first arm extender 54 is detachably coupled to an end fitting 72, located on first arm segment 13 remote from pivot end 16. The inner size and configuration of coupler 58 is such that it slides over fitting 72. Stretching out bias means 69 as shown in FIG. 8, coupler 63 on one end 62 of second arm extender 56 is detachably coupled to an end fitting 73, located on second arm segment 17 remote from pivot end 19. Coupler 58 and fitting 72 and coupler 63 and fitting 73, are preferably sized so they will only mate with each other, so that the alignment arm 12 and the arm extenders 54 and 56, can only be assembled one way. As is evident in FIGS. 7 and 8, first arm extender 54 is substantially in axial alignment with first arm segment 13, and second arm extender 56 is substantially in axial alignment with second arm segment 17. The cords 71 of resilient bias means 69 are dressed around knobs 44, ensuring a clean splint structure as the arm extenders are pulled into engagement with alignment arm 12. (See, FIG. 11).

Other features designed to extend the length and adaptability of the splint apparatus 11 include a first end pad 74 and a second end pad 76. First end pad 74 includes a foam padded portion 77, a shaft 78, and an end coupler 79. Coupler 61 includes a resiliently biased finger 81 which engages apertures 82 to secure end pad 74 to the splint assembly 11 in a selected longitudinal position. First end pad 74 is thereby adapted, adjustably and detachably, to interconnect with coupler 61 on first arm extender 54. Second end pad 76 includes a foam padded portion 83, a shaft 84, and a plurality of resiliently biased protuberances 86 spaced along shaft 84. Coupler 66 includes an aperture 87 sized and located for engagement by protuberances 86. Second end pad 76 is thereby adapted, adjustably and detachably, to interconnect with coupler 66 on second arm extender 56 at a selected longitudinal location at the end of splint apparatus 11.

First end pad 74 and second end pad 76, both include means for rotational adjustment of their respective foam padded portions 77 and 83. As shown in FIGS. 9 and 10, foam padded portions 77 and 83 may be rotated into a selected location about the axis of their respective supporting shafts. This feature allows the medical personnel to adjust these end pads into a location which will be most effective and comfortable, when the splint apparatus is fitted to the patient.

The resulting custom fitted splint apparatus 11 is carefully lowered over the patient, and arranged in alignment with the injured limb. The medical personnel then employs a plurality of flexible, resilient, and adjustable cravats 88, having different lengths and widths. These cravats are passed over and around the splint apparatus 11 and adjacent portions of the patient's body, above and below the injured critical area, to secure the splint to the patient. The outer surface 89 of the cravats is provided with a dynamic composite elasticized loop fabric, marketed under the trademark BREATH-O-PRENE™. The inner surface 91 is provided with an opened cell foam material, embedded with nano-crystals of silver to provide bacteriostatic and bactericidal qualities to the cravats. For the purpose of securing the cravats around the limb and the modeled splint apparatus 11, one end of each cravat 88 includes a short strip of hook VELCR® sewn thereon. These cravats 88 create a quick, secure closure member, binding the injured limb to the rigid structure of the splint apparatus 11.

Treatment of a straight knee injury or a dislocated knee injury may call for a special adaptation of the splint apparatus 11. For example, in FIG. 15, the splint apparatus has been fitted on one end with an ischio-perineal cushion 93, including a receiver 94. As shown in FIG. 14, coupler 66 is inserted into receiver 94, thereby securing the cushion 93 to the splint apparatus. Cushion 93 includes a hinged, adjustability feature, described in more detail in U.S. Pat. No. 4,941,465, hereby incorporated by reference as if fully set forth herein. The medical personnel applies the modified apparatus to the patient, seating the ischio-perineal cushion against the ischio-perineal protuberances of the pelvis. Cravats 88 are selectively applied around the splint apparatus 11 and the patient's leg, both above and below the knee injury.

It is also possible to eliminate the use of the alignment arm 12 altogether, by simply sliding first arm extender 54 into second arm extender 56. This can be done easily, as couplers 58 and 63 are sized and configured to mate. This mated configuration is shown in FIG. 2. This arrangement, in combination with the ischio-perineal cushion 93 on one end of the splint, and a first end pad 74 on the other end of the splint, would be appropriate when the it is desired to have an entirely straight splint apparatus.

It should also be noted that with the exception of special applications requiring use of the ischio-perineal cushion 93, the splint apparatus 11 is end-to-end reversible. In other words, the splint can be used placing the second arm extender 56 and the second end pad 76 in a proximate relationship with respect to the patient's body, as shown in FIGS. 16 and 17, or in a distal relationship with respect to the patient's body, as shown in FIG. 13.

The portable splint apparatus 11 of the present invention is preferably carried in a cordura case 96. Case 96 is capable of housing as a kit 97, all of the components necessary to make a wide variety of splint structures in a compact and easily accessible manner. In addition to the components discussed above, the kit 97 may also include a traction device 98, for applying a predetermined amount of pulling tension to the splint. For that purpose, traction device 98 includes a coupler 99 on its end, adapted to engage with coupler 61 on the end of first arm extension 54. In other words, the second end pad is replaced with the traction device 98. In addition, such an arrangement would require a straight line splint, and would not rely upon use of the alignment arm 12. Typically, this arrangement may be employed where the patient's injury is a fractured femur.

It will be appreciated, then, that I have disclosed an articulated alignment arm which is used in conjunction with associated extensions and accessories, to create a custom splint apparatus. This splint assumes the exact configuration and orientation of the injured limb in the position found by medical personnel. The splint apparatus fits closely to the silhouette of the fractured limb and becomes and excellent tool for removing injured patients from confined spaces. The splint apparatus disclosed herein will fit any adult or child, any size, any weight, and can be used to splint any limb injury, including fracture dislocations of the shoulder, elbow, knee and ankle.

What is claimed is:

1. An articulated alignment arm for modeling the orientation of an injured human limb comprising:
  a. a first elongated arm segment having a longitudinal axis and a respective pivot end, said pivot end including a first segment disc portion, a first segment pivot aperture, and a plurality of ribs extending radially from said first segment pivot aperture on said first segment disc portion;
  b. a second elongated arm segment having a longitudinal axis and a respective pivot end said pivot end including a second segment disc portion, a second segment pivot aperture, and a plurality of ribs extending radially from said second segment pivot aperture on said second segment disc portion;
  c. a connector body for interconnecting said first arm segment to said second arm segment, said connector body including a first receiver having a first receiver disc portion, a first receiver pivot aperture, and a plurality of ribs extending radially from said first receiver pivot aperture on said first receiver disc portion, said first segment disc portion overlying said first receiver disc portion, and a second receiver, having a second receiver disc portion, a second receiver pivot aperture, and a plurality of ribs extending radially from said second receiver pivot aperture on said second receiver disc portion, said second segment disc portion overlying said second receiver disc portion;
  d. first fastening means passing through said first segment pivot aperture and said first receiver pivot aperture, for drawing said ribs on said first segment disc portion and said first receiver disc portion together, and locking said first arm segment at a first selected orientation about a first axis;
  e. second fastening means passing through said second segment pivot aperture and said second receiver pivot aperture, for drawing said ribs on said second segment disc portion and said second receiver disc portion together, and locking said second arm segment at a second selected orientation about a second axis, said first axis and said second axis being perpendicular with respect to each other.

2. An alignment arm as in claim 1 in which said first fastening means comprises a shaft having a knob on one end, a resilient barb on the other, and threads therebetween, said first fastening means further including threads in at least one aperture, of either said first receiver pivot aperture or said first segment pivot aperture, in a location remote from said knob.

3. An alignment arm as in claim 1 in which said second fastening means comprises a shaft having a knob on one end, a resilient barb on the other end, and threads therebetween, said second fastening means further including threads in at least one aperture, of either said second receiver pivot aperture or said second segment pivot aperture in a location remote from said knob.

4. An alignment arm as in claim 1 further including at least one elongated arm extender, said arm extender having one end being detachably coupled to an end of one of said arm segments remote from said pivot end and being substantially in axial alignment therewith.

5. An alignment arm as in claim 4 in which said arm extender is padded substantially around and along its length.

6. An alignment arm as in claim 1 including a first elongated arm extender and a second elongated arm extender, each said arm extender having one end and another end, said one end of each being interconnected to said one end of the other by resilient and flexible bias means for drawing said arm extenders together, said one end of said first arm extender being detachably coupled to an end of said first arm segment remote from said pivot end and being substantially in axial alignment therewith, and said one end of said second arm extender being detachably coupled to an end of said second arm segment remote from said pivot end and being substantially in axial alignment therewith.

7. An alignment arm as in claim 6 further including first and second end pads, said first and second end pads each including a padded portion and being adapted to detachably couple with a respective said another end of said first and second arm extenders.

8. An alignment arm as in claim 7 in which each of said end pads has an axis, and in which said padded portion of said end pads is selectively rotatable about a respective said axis of said end pads.

9. An articulated alignment arm for modeling the orientation of an injured human limb comprising:
   a. a first elongated arm segment having a longitudinal axis and a respective pivot end;
   b. a second elongated arm segment having a longitudinal axis and a respective pivot end;
   c. a connector body for interconnecting said first arm segment to said second arm segment, said connector body including a first receiver adapted to couple with said respective pivot end of said first arm segment and lock said first arm segment at a first selected orientation about a first axis, and a second receiver adapted to couple with said respective pivot end of said second arm segment and lock said second arm segment at a second selected orientation about a second axis, said first axis and said second axis being perpendicular with respect to each other; and,
   d. a first elongated arm extender and a second elongated arm extender, each said arm extender having one end and another end, said one end of said first arm extender being detachably coupled to an end of said first arm segment remote from said pivot end and being substantially in axial alignment therewith, and said one end of said second arm extender being detachably coupled to an end of said second arm segment remote from said pivot end and being substantially in axial alignment therewith.

10. An alignment arm as in claim 9 further including first and second end pads, said first and second end pads each including a padded portion and being adapted to detachably couple with a respective said another end of said first and second arm extenders.

11. A kit for assembling splints in the field, comprising:
   a. a carrying case;
   b. an articulated alignment arm in said carrying case for modeling the orientation of an injured human limb including: a first elongated arm segment having a longitudinal axis and a respective pivot end; a second elongated arm segment having a longitudinal axis and a respective pivot end; a connector body for interconnecting said first arm segment to said second arm segment, said connector body including a first receiver adapted to couple with said respective pivot end of said first arm segment and lock said first arm segment at a first selected orientation about a first axis, and a second receiver adapted to couple with said respective pivot end of said second arm segment and lock said second arm segment at a second selected orientation about a second axis, said first axis and said second axis being perpendicular with respect to each other;
   c. a first elongated arm extender and a second elongated arm extender in said carrying case, each said arm extender having one end and another end, said one end of said first arm extender being detachably coupled to an end of said first arm segment remote from said pivot end and being substantially in axial alignment therewith, and said one end of said second arm extender being detachably coupled to an end of said second arm segment remote from said pivot end and being substantially in axial alignment therewith;
   d. first and second end pads in said carrying case, said first and second end pads each including a padded portion and being adapted to detachably couple with a respective said another end of said first and second arm extenders;
   e. a plurality of flexible and resilient cravats in said carrying case, each said cravats having one end with means for detachably connecting an exposed surface of a respective cravat.

12. A kit as in claim 11 further including in said carrying case, means for providing traction between a stationary part and a moveable part, said means for providing traction including a coupler for attachment of said stationary part to said other end of said first arm extender, and a base cushion including a coupler for attachment to said other end of said second arm extender.

13. A method for creating and applying a splint structure which models the configuration of an injured patient's limb, comprising the steps of:
   a. providing an articulated, adjustable, and lockable alignment arm, said alignment arm having a connector body with ends pivotally attached to one end of first and second elongated arm segments, said arm segments being rotationally adjustable and lockable into selected rotational positions about respective perpendicular pivotal axes;
   b. locating said alignment arm over the injured limb of the patient;
   c. adjusting said alignment arm to form a structural model which emulates the shape of the injured limb of the patient;
   d. locking said first and second arm segments of said structural model into respective fixed relations with respect to said connector body;
   e. coupling first and second elongated arm extenders respectively with the other ends of said first and second arm segments, so that said first arm extender and said first arm segment are substantially in axial alignment, and that said second arm extender and said second arm segment are substantially in axial alignment;
   f. positioning said alignment arm fitted with said first and second arm extenders over the injured limb of the patient; and,
   g. wrapping flexible cravats completely around said first and second arm extenders and a respective underlying portion of the injured limb of the patient, securing and applying the splint structure to the limb.

14. A method as in claim 13 further including the steps of coupling first and second arm end pads to said first and second arm extenders, and wrapping flexible cravats completely around said first and second arm end pads and a respective underlying portion of the injured limb of the patient, further securing the splint structure to the limb.

15. A method as in claim 13 in which the injured limb of the patient is a leg.

16. A method as in claim 13 in which the injured limb of the patient is an arm.

17. A method as in claim 13 in which the injured limb of the patient is a foot.

18. A method as in claim 13 in which the injured limb is a leg and the injury is to the knee of the leg.

* * * * *